United States Patent [19]
Schwarz et al.

[11] Patent Number: 5,437,998
[45] Date of Patent: Aug. 1, 1995

[54] GAS PERMEABLE BIOREACTOR AND METHOD OF USE

[75] Inventors: Ray P. Schwarz, Friendswood; Frederick A. Archibald, III, Clear Lake Shores, both of Tex.

[73] Assignee: Synthecon, Inc., Houston, Tex.

[21] Appl. No.: 118,512

[22] Filed: Sep. 9, 1993

[51] Int. Cl.⁶ .................. C12M 1/04; C12M 1/10; C12M 3/02
[52] U.S. Cl. .................. 435/286; 422/209; 422/239; 435/240.24; 435/240.25; 435/240.46; 435/296; 435/312; 435/313; 435/818
[58] Field of Search ............ 435/240.25, 240.46, 435/286, 312, 818, 240.24, 296, 313; 422/130, 239, 209

[56] References Cited

U.S. PATENT DOCUMENTS

| | | | |
|---|---|---|---|
| 3,676,074 | 7/1972 | Shibayama et al. | 422/209 |
| 3,827,943 | 8/1974 | Mann | 435/312 |
| 3,925,165 | 12/1975 | Müller | 195/127 |
| 4,244,916 | 1/1981 | Guigan | 422/72 |
| 4,343,904 | 8/1982 | Birch et al. | 435/240 |
| 4,435,508 | 3/1984 | Gabridge | 435/284 |
| 4,535,062 | 8/1985 | Müller | 435/289 |
| 4,846,786 | 7/1989 | Freed et al. | 604/4 |
| 4,988,623 | 1/1991 | Schwarz et al. | 435/286 |
| 5,010,014 | 4/1991 | Gebhardt | 435/289 |
| 5,026,650 | 6/1991 | Schwarz et al. | 435/286 |
| 5,153,131 | 10/1992 | Wolf et al. | 435/240.25 |
| 5,153,132 | 10/1992 | Goodwin et al. | 435/240.24 |
| 5,153,133 | 10/1992 | Schwarz et al. | 435/240.24 |
| 5,155,034 | 10/1992 | Wolf et al. | 435/240.24 |
| 5,155,035 | 10/1992 | Schwarz et al. | 435/240.24 |
| 5,330,908 | 7/1994 | Spaulding | 435/240.25 |

FOREIGN PATENT DOCUMENTS

| | | | |
|---|---|---|---|
| 0164888 | 12/1985 | European Pat. Off. | C12M 3/02 |
| 264464 | 4/1988 | European Pat. Off. | 435/296 |

*Primary Examiner*—Jeffrey E. Russel
*Attorney, Agent, or Firm*—John R. Casperson; Buskop Law Group

[57] ABSTRACT

A new rotating cell vessel and method of use have been developed. The vessel is constructed of materials which are permeable to oxygen and carbon dioxide, and when rotated horizontally suspend the contents, cells and particle substrates, in a liquid medium with a low turbulence, low shear fluid environment. The vessel walls are made at least partially of gas permeable material. The vessel is rotated in a horizontal plane to suspend the cells and substrate particles in a low turbulence liquid nutrient medium. Oxygen continuously diffuses through the permeable vessel material and through the cell culture liquid medium to provide the needed oxygen to the cells. Carbon dioxide diffuses through the cell culture medium and through the vessel wall, removing this waste product from the cell culture. The vessel is uniquely designed to be simply constructed.

9 Claims, 3 Drawing Sheets

GAS PERMEABLE BIOREACTOR AND METHOD OF USE

BACKGROUND OF THE INVENTION

This invention relates to an apparatus and method of use for a new simply constructed bioreactor made at least partially of gas permeable materials. The bioreactor is useful for culturing cells and tissues in suspension in a liquid nutrient medium with minimum turbulence. The bioreactor may include ports for easy access to the vessel culture, allowing the growth substrate to be varied for optimum performance.

A primary use is in research where large numbers of cells are grown to refine the minute quantities of an active material (e.g., proteins) that the cells might secrete. Another use of bioreactors is the scale-up of laboratory cell culture processes for commercial purposes to mass produce the active proteins made by genetically engineered cells. Because of the need to culture mammalian cells in the laboratory in large quantities, bioreactors have become an important tool in research and production of cells that produce active proteins.

A current problem in tissue culture technology is the unavailability of an inexpensive bioreactor for the in vitro cultivation of cells and explants that allows easy access to the materials contained in the vessel. Several devices presently on the market have been used with considerable success, but each has its limitations which restrict usefulness and versatility.

Cell culturing devices range upward in complexity from the petri dish, to plastic flasks, to sophisticated computer controlled bioreactors. In the past, manufacturers have promoted various technologies to culture cells in the laboratory. Simple adaptations of fermentors (stirred tanks) used for the culture of bacteria were marketed previously as the answer to culturing delicate mammalian cells. One of the principal factors limiting the performance of these systems is their inability to minimize turbulence due to stirring, i.e., shear due to fluid flow, and hence preventing free form association of cells in three dimensions.

Another utilized technology is microcarrier cell culture, which involves the use of substrate particles, generally collagen-coated beads, to culture anchorage dependent cells. Bioreactors for microcarrier or suspension cells must suspend the cells and substrate in a fluid medium. In the past, this generally was done with an impeller in a stirred tank. Oxygen was provided by sparging (i.e., bubbling) air through the liquid medium. Both the impeller and the bubbling air, unfortunately, create turbulence.

In recent years, a variety of devices have been designed involving horizontal rotating vessels for the suspension of solids in liquid slurries, including bioreactors for cell culture. The primary inventor of the present invention was a co-inventor on six prior patents involving bioreactor systems or methods. They are as follows: U.S. Pat. No. 5,155,035, Schwarz, et al., "Method For Culturing Mammalian Cells In A Perfused Bioreactor" issued Oct. 13, 1992; U.S. Pat. No. 5,155,034, Wolf, et al., "Three-Dimensional Cell To Tissue Assembly Process" issued Oct. 13, 1992; U.S. Pat. No. 5,153,133, Schwarz, et al., "Method For Culturing Mammalian Cells In A Horizontally Rotated Bioreactor", issued Oct. 6, 1992; U.S. Pat. No. 5,153,131, Wolf, et al., "High Aspect Vessel And Method Of Use", issued Oct. 6, 1992; U.S. Pat. No. 5,026,650, Schwarz, et al., "Horizontally Rotated Cell Culture System With A Coaxial Tubular Oxygenator", issued Jun. 5, 1991; and U.S. Pat. No. 4,988,623, Schwarz, et al., "Rotating Bio-Reactor Cell Culture Apparatus", issued Jan. 29, 1991. These patents are incorporated herein by reference as if set out fully verbatim. U.S. Pat. No. 5,153,132, Goodwin, et al., "Three-Dimensional Co-Culture Process", issued Oct. 6, 1992, is closely related to this group of patents, and is also incorporated herein fully as if set out verbatim.

These prior patents disclose apparatuses that use either an internal cylindrical oxygenator or a flat disk shaped oxygenator membrane inserted internally between two pieces of the vessel. Both types of vessels require oxygen injectors.

Specifically, U.S. Pat. Nos. 4,988,623; 5,153,133; and 5,155,034 disclose culture vessels, allowing three-dimensional cell growth, that are shaped similarly to each other due to a central tubular member that functions as a membrane to allow air to be injected through the tubular membrane and into the fluid medium. These patents also disclose internal circularly disposed sets of blade members that rotate around the central horizontal axis, to move the fluid medium within the culture vessel. The apparatus disclosed in U.S. Pat. No. 5,026,650 is similar to the first three patents, but does not contain the blades that move the fluid medium.

U.S. Pat. No. 5,153,131 discloses a bioreactor vessel without mixing blades or a central tubular membrane. This apparatus still requires injection of air into the bioreactor vessel. Air travels through an air inlet passageway, through a support plate member, through a screen and filter cloth, and through a flat disk permeable membrane wedged between the two sides of the vessel housing. The construction of either the tubular membrane or the flat disk one is expensive in terms of the raw materials used (silicone rubber) and the manufacturing process. These membranes are delicate, difficult to install, and require servicing and testing to insure they are free of leaks. A single small hole in the membrane admits air in minute quantities, which forms into air bubbles. As mentioned above, even one air bubble causes damaging turbulence which inhibits or prevents cell growth.

Furthermore, the flat disk membrane in U.S. Pat. No. 5,153,131 flexes to cause mixing(col. 8,line 63 to col. 9, line 5), which is stated to be critical for the distribution of air throughout the culture media. This mixing effect, however, disrupts three dimensional cell growth. The simulation of the zero gravity environment that this design supposedly offers is incomplete because membrane flexing would not occur in a truly zero gravity environment, such as aboard the Space Shuttle in orbit around the earth. Consequently, an improved method of suspending particles(cells and their substrate) that minimizes fluid turbulence, while at the same time providing the required oxygen transfer, is needed to improve the performance of bioreactors. It is an object of the present invention to provide both an apparatus and a method for culturing cells that overcomes the technological limitations of prior bioreactor systems.

SUMMARY OF THE INVENTION

The present invention is directed to a new class of bioreactor for cell culture and a method for use of the bioreactor, whereby the preferred embodiment of the apparatus is a gas permeable bioreactor comprising a tubular vessel with walls constructed at least partially of a gas permeable material. The tubular vessel has closed ends, a substantially horizontal longitudinal central axis, and one or more vessel access ports for transferring materials into and out of the tubular vessel. Means is provided for rotating the vessel about its horizontal longitudinal central axis.

In another preferred embodiment of the apparatus of this invention, the gas permeable bioreactor is a tubular vessel with walls constructed at least partially of a gas permeable material. It has closed ends, a substantially horizontal longitudinal central axis, and is constructed of two sliding members. A first sliding member fits slidably into a second sliding member, forming a liquid tight seal therebetween. The vessel also has means for rotating it about its horizontal longitudinal central axis. One or more access ports are provided on the vessel for transferring materials into and out of said vessel.

An alternative embodiment of the bioreactor of the present invention is an annular vessel with walls constructed at least partially of a gas permeable material. The annular vessel has closed ends, which leaves the central portion of the vessel open. The annular vessel rotates around a substantially horizontal longitudinal central axis and has means for rotating the vessel. One or more access ports are provided for transferring materials into and out of the vessel.

The bioreactor of the present invention is constructed at least partially of a gas permeable material, such as, but not limited to, silicone rubber, polytetrafluoroethylene (teflon ®, a registered mark of DuPont), polyethylene, porous polytetrafluoroethylene, other porous plastics, porous plastics coated with a hydrophobic material, mixtures of silicone rubber with other plastics, or silicone rubber coated cloth. In one preferred embodiment of the present invention the vessel is formed of injection molded gas permeable plastic.

It is an object of the present invention to provide a bioreactor vessel that uses only horizontal rotation (clinostatic suspension) to suspend particles in a culture vessel. This is an advantage over the prior art, which required stirring or mixing for particle suspension and oxygenation. The bioreactor of this invention, in contrast, provides a very low turbulence regime. The present invention also overcomes the prior art need for air injection into the bioreactor vessel. The use of air injection is not excluded from the present invention, however. The gas permeable material of which the bioreactor of this invention is constructed provides this advantage by allowing $O_2$ to diffuse through the vessel walls and into the cell culture media in the vessel chamber. Correspondingly, $CO_2$ diffuses through the walls and out of the vessel. Clinostatic suspension combined with oxygenation by diffusion merges ideal properties for a high performance bioreactor vessel.

It is another object of the present invention to provide a bioreactor vessel that is disposable. Due to the present bioreactor's simple design and construction, it can be easily and economically manufactured. The resulting bioreactor is consequently affordable, disposable, and may be mass produced. In situations where minimization of contamination is necessary (e.g., AIDS or human tissue research), disposability of the bioreactor is a particular advantage. While the bioreactor may be produced in a wide variety of sizes, its simple construction provides the advantage of allowing bioreactors to be made smaller than previously possible. The smaller sizes are helpful in research laboratories, in particular. Moreover, the embodiment of the bioreactor with two slidably interconnected members may be adjusted to provide the exact size bioreactor needed.

Another aspect of the present invention is a method for growing cells in a gas permeable bioreactor. The method involves filling a bioreactor constructed at least partially of a gas permeable material with a liquid culture medium and cells; suspending said cells, without appreciable mixing, in the cell medium by rotating the bioreactor about its horizontal longitudinal central axis at a rate that suspends the cells in the liquid culture medium. The rotation is continued for a time period to permit desired cell growth. An alternative embodiment of the method of this invention includes adding a growth substrate, such as substrate particles or tissue explants, to the bioreactor with the culture medium and cells.

Still other objects, features and advantages of the present invention will be apparent from the following description of the preferred embodiments given for the purpose of disclosure and taken in conjunction with the accompanying drawings.

DESCRIPTION OF THE PREFERRED EMBODIMENT

Figure 1:
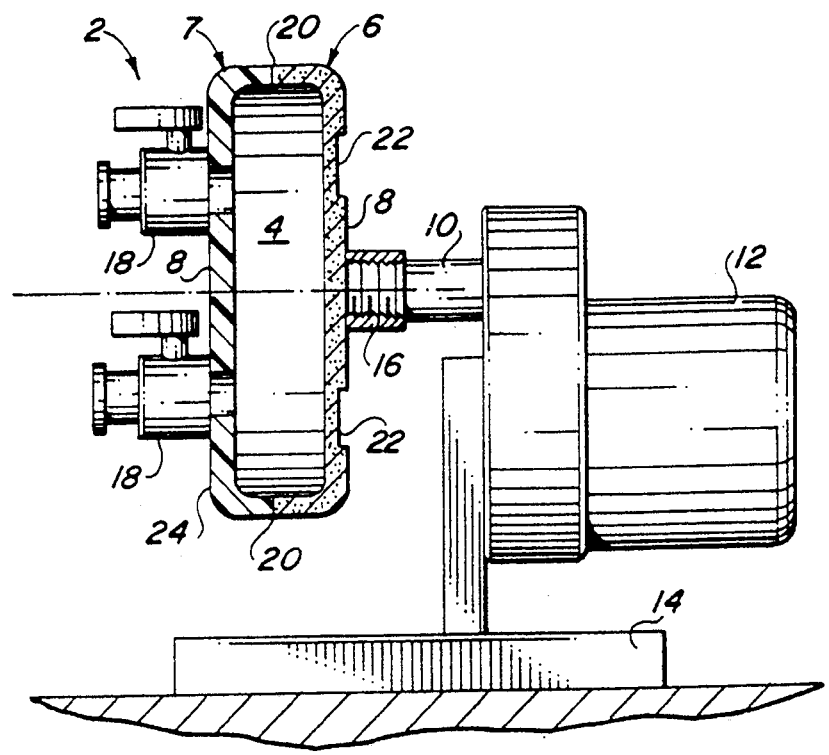
FIG. 1 is a partially cross-sectional side view of a preferred embodiment of the gas permeable bioreactor of the present invention showing attachment to a motor assembly unit for rotation purposes and showing a cross-section of the bioreactor vessel.

Referring to the drawings, FIG. 1 is a cross-sectional side view of a preferred embodiment of the gas permeable bioreactor of the present invention showing a motor assembly unit for rotation purposes. In the preferred embodiment of the invention, the bioreactor 2 is made of a tubular vessel 4 with outer walls 24 constructed at least partially of a gas permeable materials 6 definig a vessel chamber. The walls 24 themselves may be constructed of the gas permeable material 6 or the material 6 may be made a part of the walls 24 in the same manner as the microscope viewports 50 discussed below. The vessel 4 has closed ends 8 and a substantially horizontal longitudinal central axis 10. One or more vessel access ports 18 are provided for transferring materials into and out of the vessel 4. The vessel 4 in one preferred embodiment is constructed such that half of it is comprised of gas permeable material 6 and the remaining portion is made of nonpermeable material 7.

The gas permeable materials 6 commonly available are opaque. Thus, using nonpermeable material 7 for part of the bioreactor 2 may provide an advantage in allowing visual inspection of the tubular vessel chamber. To further enhance oxygen absorption into the tubular vessel chamber, depressions 22 may be formed in the walls 24 in areas where there is gas permeable material 6. The thinner the wall 24, the less distance the oxygen must travel before entering the tubular vessel chamber. The gas permeable material 6 used to make the bioreactor 2 preferably is a porous, hydrophobic material. It may be a porous nonhydrophobic material coated on one side with silicone rubber or some other hydrophobic material to achieve gas permeability. However, if the pore size of the porous material is one micron or less, a coating is not preferred. In the preferred embodiment, the porous material used is a "foamed" plastic, which is a hardened porous plastic. This porous plastic is available commercially in a variety of pore sizes from companies such as Porex Technologies (located in Fairburn, Ga.). For instance, Porex manufactures products in porous polytetrafluoroethylene and polyethylene that are suitable for use in this invention.

Any nonpermeable material 7 used to construct the walls 24 preferably is a transparent, nontoxic, biocompatible material such as clear plastic. Most preferably the clear material is polycarbonate (also known as Lexan ®, a registered trademark of General Electric).

The bioreactor 2, furthermore, may be made of a variety of materials: silicone rubber, polytetrafluoroethylene, polyethylene, porous plastic, porous plastic coated with a hydrophobic material, mixtures of silicone rubber with other plastics, and silicone rubber coated cloth. Preferably, the bioreactor 2 is constructed of porous plastic coated with a hydrophobic material on the interior surface. Most preferably, the vessel 4 is made of porous hydrophobic teflon. The vessel 4 may also be formed out of injection molded plastic. When injection molded plastic is used, the molded pieces of the tubular vessel 4 may be welded, glued, or mechanically attached together. Preferably, the tubular vessel is made in two pieces which are welded, glued, or mechanically attached together around a circumferential seam 20, as shown in FIG. 1. Other construction methods may be used, however, such that the tubular vessel 4 may be formed of one piece of molded plastic, thus eliminating the circumferential seam 20. The bioreactor 2 is constructed at least partially of a gas permeable material 6, and the percentage of the tubular vessel made of gas permeable material may vary from about 5% to about 100%. In one preferred embodiment of the bioreactor 2, the vessel 4 is constructed with a first half comprised of gas permeable material 6 and a second half comprised of a non-gas permeable material 7.

The tubular vessel 4 may be made in any size, so long as the surface area to volume ratio of the tubular vessel 4 is large enough to allow adequate gas transfer through the walls 24 to the cell culture in the tubular vessel 4. As a tubular vessel 4 gets larger (by expanding all dimensions proportionally) the volume increases as the cube of its dimensions, whereas the surface area increases as the square of its dimensions. Once a certain size is reached, the reduced surface area per volume will hinder adequate gas transfer. This can be avoided, however, by scaling up the size in one dimension only. For instance, the length of the tubular vessel may be increased but not the diameter, or the diameter may be increased but not the length. For tubular vessels of a size of 500 ml or less, the dimensions of the tubular vessel 4 are not critical.

Additionally, the dimensions and shapes of the tubular vessels 4 are use dependent. The type of cells being grown and the use of substrate carriers affects gas transfer. When the suspension cells are lightweight, they cause little mixing and oxygen must travel further from the wall 24 to the cells. When larger cell colonies are grown on substrate carriers, mixing results such that less gas transfer is required for oxygenation of the cells. The acceptable variations of the dimensions are endless, but those skilled in the art will be able to adjust the dimensions to suit the particular application, while still providing adequate $O_2$ transfer.

In the preferred embodiment of the invention, the volumetric size of the tubular vessel chamber 4 is preferably in the range of about 1 ml to about 500 ml. The diameter of the tubular vessel 4 preferably is in the range of about 1 inch to about 6 inches. The most preferred range of diameters is in the range of about 3 inches to about 6 inches.

The width of the bioreactor 2, due to the permeability of the walls 24, may be doubled relative to widths in prior art designs, since gas can be transferred from all tubular vessel surfaces. For cells in free suspension (very small particles which do not settle quickly) the preferred chamber width is about $\frac{1}{4}$ inch but may be in the range of about $\frac{1}{8}$ inch to about 1 inch. While the volume of the tubular vessel chamber may be any size, it should be kept in mind that the bioreactor 2 produces at least 10 to 20 million cells per milliliter. Thus, a tubular vessel 4 of 2.0 liters would allow growth of approximately 20 billion cells. An advantage of this productivity, is that smaller tubular vessels 4 may be used than ever before.

A preferred means for rotation is a motor assembly 12 as shown in FIG. 1. The motor assembly 12 sits on a mounting base 14 and has means 16 for attachment to the tubular vessel 4. Preferably, the means for attachment 16 comprises threadably connecting the tubular vessel 4 to the motor assembly 12 through screw threads on the drive shaft corresponding to screw threads on the tubular vessel 4. Preferably, these screw threads are in a direction such that inadvertent loosening of the tubular vessel 4 from the motor assembly 12 due to the movement of rotation is avoided. In addition, a lock nut or similar device may be provided on the drive shaft to prevent unscrewing. In the preferred embodiment, a $\frac{3}{8}$ inch threaded shaft coupling is used, but this may be varied to coordinate with the size of the bioreactor 2.

Figure 8:
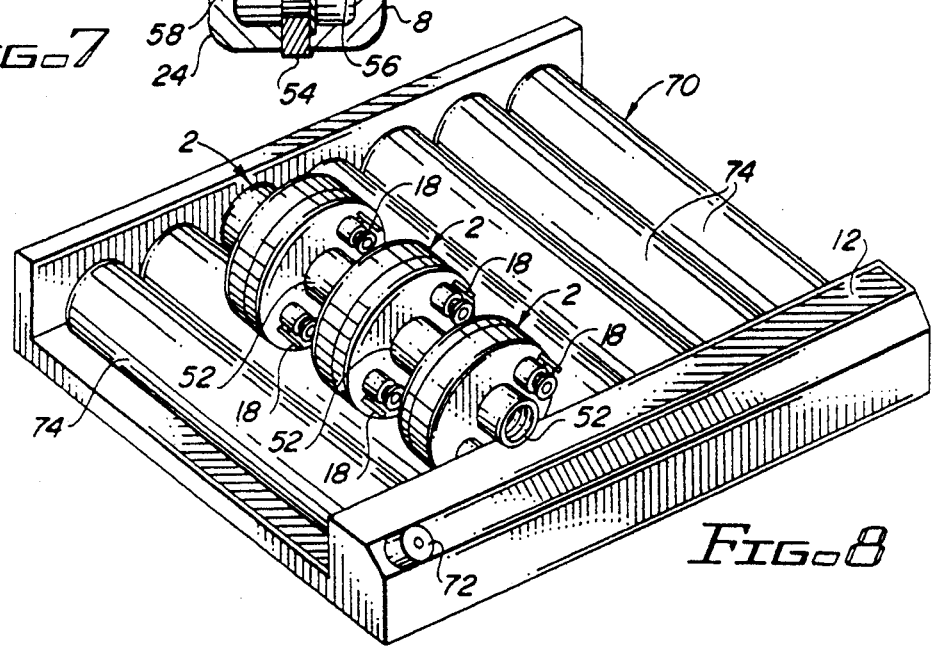
FIG. 8 is a perspective view of a preferred embodiment of a roller mechanism used to rotate one or more bioreactors, showing three bioreactors attached end-to-end and rotating thereon.

The means for rotation in one preferred embodiment is a roller mechanism 70 as shown in FIG. 8. The roller mechanism 70 has multiple rollers 74 stretched longitudinally in a horizontal plane which rotate simultaneously to correspondingly rotate any bioreactor 2 laid on the roller mechanism 70. Such roller mechanisms 70 are commercially available. The bioreactor 2 of the present invention may be rotated on a roller mechanism 70 such as the ones produced by Stoval Life Science, Inc. Stoval manufactures compact, nondedicated roller units which perform multiple functions in the biological research laboratory. It operates on benchtops, in high humidity and carbon dioxide incubators, high temperature ovens (to 65° C.), and in refrigerated units (0° C.). The roller mechanism 70 has speed control operated by a speed control knob 72. Other roller mechanisms 70, of course, may be utilized as will be commonly known to those skilled in the art. The bioreactor 2 of the present invention may also be constructed with means 52 on each end 8 for attaching one tubular vessel 4 to an additional tubular vessel 4, thereby creating a chain of bioreactors 2. One or more vessel access ports 18 are provided for transferring materials into and out of the tubular vessel chamber 4.

The preferred speed of rotation is in the range of about 2.0 rpms to about 40 rpm and is largely dependent on the specific bioreactor and what is being cultured. For example, for a bioreactor of about 3 to 5 inches in diameter, with a width of about 0.25 inches, growing BHK-21 cells in a microcarrier culture, the preferred speed of rotation is about 24 rpm. Speed must be adjusted to balance the gravitational force against the centrifugal force caused by the rotation. For tubular vessels of up to about 5 inches in diameter, the rotational speed may range from about 2 rpm for single cells in suspension, up to about 40 rpm for large particles grown on microcarrier substrates.

As shown in FIG. 1, the vessel access ports 18 provide access to the bioreactor 2 for input of medium and cells and for removal of old medium from the tubular vessel 4. This is easily done through the vessel access ports 18, which are also referred to as valves or syringe ports. In the preferred embodiment, the vessel access ports 18 are constructed of valves with syringe ports. The valves preferably are plastic, but may be made of metal or any other material which is hard enough for machining into an access port and is non-toxic. The carbon dioxide produced by the cells when they use oxygen and metabolize sugar leaves the tubular vessel chamber primarily by traveling out through the gas permeable wall 24 of the tubular vessel 4.

Another advantage of the new bioreactor 2 is that air filters for the $O_2$ source are unnecessary, as previously required. The prior art bioreactors required an air filter to protect the air pump valves from dirt. The bioreactor 2 of the present invention relies on the rotation of the tubular vessel 4 to circulate fresh air over its surface.

Figure 7:
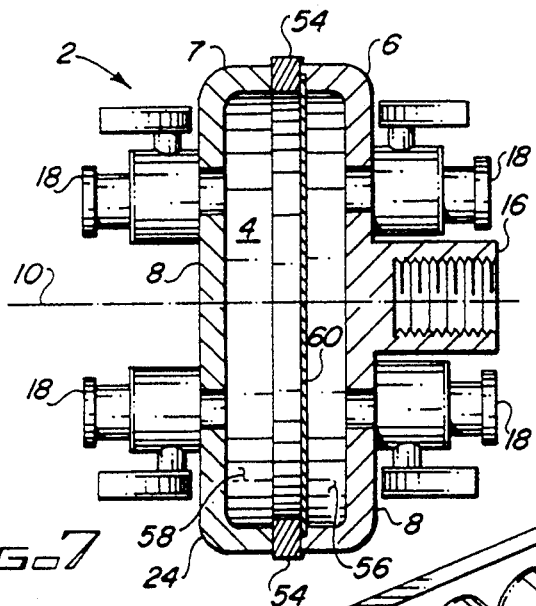
FIG. 7 is an alternative embodiment of the gas permeable bioreactor with an internal membrane dividing the vessel into two chambers, one for cell culture and one for exchanging cell medium without disturbing the cells in the other chamber.

In an alternative embodiment of the bioreactor 2, as shown in FIG. 7, a permeable membrane 60 is inserted into the tubular vessel 4 in a plane substantially perpendicular to the horizontal axis 10 to separate the tubular vessel 4 into two chambers: a cell growth chamber 58 and a reservoir chamber 56. It should be noted, however, that the two chambers 58, 56 are functionally interchangeable, i.e., either one may be used for cell growth. The cell growth chamber 58 preferably is used for cell culture. The reservoir chamber 56 may be filled and refilled with fresh medium without disturbing the cell culture in the cell growth chamber 58. The membrane 60 has a porosity that allows medium and metabolic waste to travel through it, but cells and substrates are too large to do so. Thus, this embodiment of the invention allows greater freedom in replacing the cell medium, particularly when the cell culture is producing large amounts of waste metabolites. In some past systems, it was necessary to centrifuge the cell culture to separate the cells from the medium in order to accomplish a change of the medium. This embodiment of the invention avoids the need to centrifuge the cell culture suspension.

In the preferred embodiment of the invention, the bioreactor 2 is made of a tubular vessel 4 with walls 24 constructed at least partially of a gas permeable material 6. The tubular vessel chamber 4 in one preferred embodiment is constructed such that, half of it is comprised of gas permeable material 6 and the remaining portion is made of nonpermeable material 7. The tubular vessel chamber 4 has closed ends 8, one of which is provided with a means 16 for attachment to a motor assembly not shown. In this embodiment of the invention, four vessel access ports 18 are used to allow access to the contents of the tubular vessel 4 on each side of the membrane 60. Furthermore, a seam bracket 54 between two pieces of the tubular vessel 4 may be used to attach the membrane 60 across the tubular vessel 4. Alternatively, the membrane may be glued, welded, or mechanically attached between the pieces of the tubular vessel 4.

Figure 5:
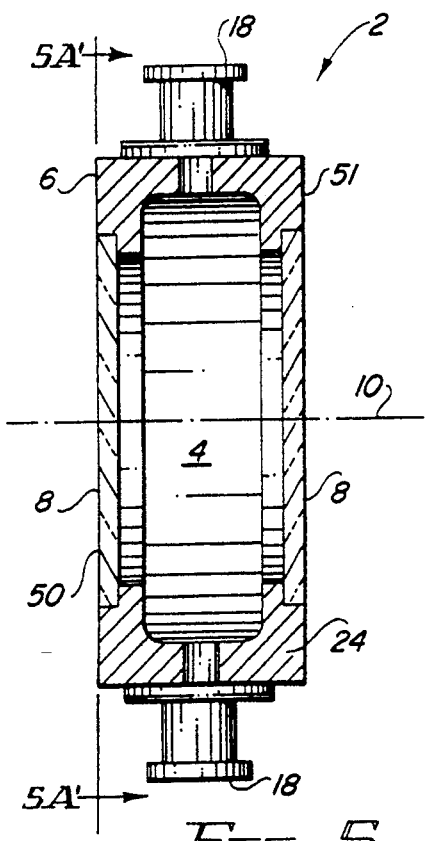
FIG. 5 is a cross-sectional side view of another preferred embodiment of the bioreactor with clear microscope viewports on each end of the vessel.
Figure 5A:
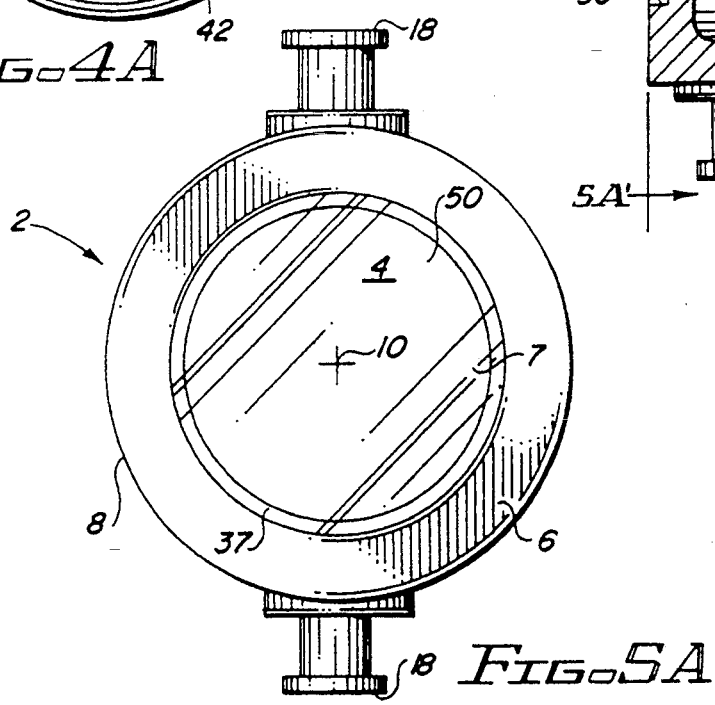
FIG. 5A is an end view of the embodiment of the tubular bioreactor of FIG. 5 taken along the line 5A'—5A'.

Another feature of the present invention is a microscope viewport 50 which may be incorporated into the walls 24. FIGS. 5 and 5A portray a bioreactor 2 of the present invention made entirely of gas permeable material 6, except for microscope viewports 50 which are incorporated on each end 8 of the tubular vessel 4. The viewports 50 may be glued, welded, or mechanically attached to the ends 8. Moreover, as shown in FIG. 5., the ends 8 may be formed to provide shoulders 51 for the viewports 50 to rest against and be attached to. Preferably, two microscope viewports 50 are incorporated into the walls 4 opposite to each other, so that the microscope will have a clear viewing path through the tubular vessel 4. FIG. 5A is an end view of the bioreactor 2 of FIG. 5 taken along the line 5A'—5A'. The tubular vessel chamber 4 in one preferred embodiment as shown in FIGS. 5 and 5A is constructed such that half of it is comprised of a gas permeable material 6 and the remaining portion is made of nonpermeable material 7. The tubular vessel chamber 4 has closed ends 8 and a substantially horizontal longitudinal central axis 10. One or more vessel access ports 18 are provided for transferring materials into and out of the tubular vessel chamber 4. In addition, a shoulder 37 may provide a resting place for the drive shaft (not shown) to rest against the connected tubular vessel 4.

Figure 6:
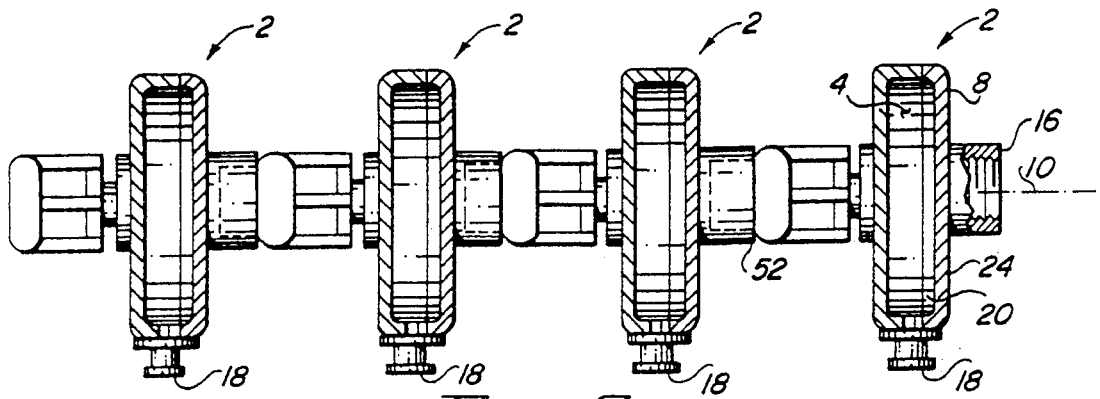
FIG. 6 is a cross-sectional partially expanded side view of an alternative embodiment of the bioreactor where multiple bioreactors are attached to each other end to end.

As shown in FIG. 6, the bioreactor 2 of the present invention may also be constructed with means 52 on each end 8 for attaching one tubular vessel 4 to an additional tubular vessel 4, thereby creating a chain of bioreactors 2. When a chain of bioreactors 2 is formed in this manner, the chain may be attached to a means for rotation at one of its ends 8. If a motor assembly is used for rotation of the chain of bioreactors 2, the vessel access port 18 may be located on the circumferential perimeter of the tubular vessel 4 for easier access. However, if the chain of bioreactors 2 as shown in FIG. 6 is to be rotated on a roller mechanism 70 as shown in FIG 8, for example, the vessel access ports 18 should be located on the tubular vessel 4 ends 8. In the preferred embodiment of the invention, and as shown in FIG. 6, the bioreactor 2 is made of a tubular vessel 4 with walls 24 constructed at least partially of a gas permeable material 6. The tubular vessel chamber 4 has closed ends 8 and a substantially horizontal longitudinal central axis 10. The tubular vessel 4 has means 16 for attachment to a motor assembly, not shown. Preferably, the tubular vessel 4 is made in two pieces which are welded, glued, or mechanically attached together around a circumferential seam 20.

Figure 2:
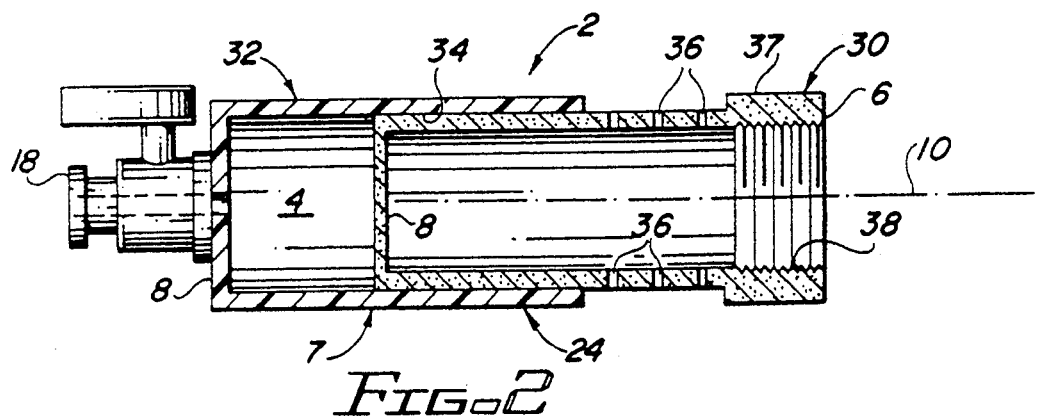
FIG. 2 is a cross-sectional side view of another preferred embodiment of the bioreactor having two slidably interconnected members to provide a variable volume vessel. The bioreactor is shown in the open position.
Figure 3:
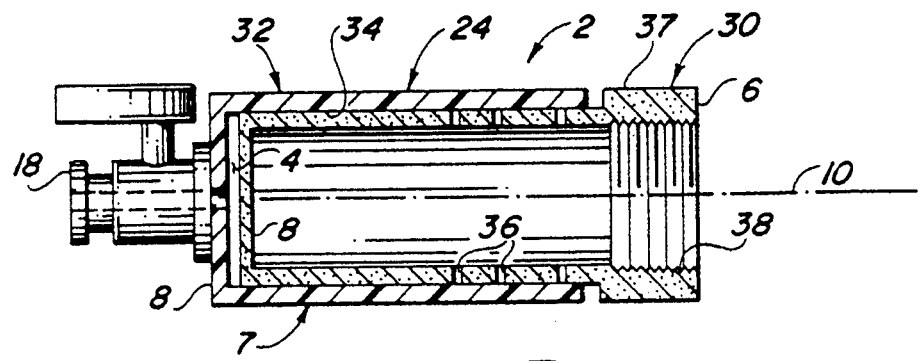
FIG. 3 is a cross-sectional side view of the bioreactor shown in FIG. 2 in the closed position.

The present invention also includes a bioreactor 2 with a variable volume, as shown in FIGS. 2 and 3. In this embodiment of the bioreactor 2, the bioreactor 2 is comprised of a tubular vessel 4 constructed at least partially of a gas permeable material 6. The vessel 4 has closed ends 8 and a substantially horizontal longitudinal central axis 10 around which it rotates. The vessel 4, furthermore, has two slidably interconnected members 30, 32, wherein a first member 30 fits slidably into a second member 32, forming a liquid tight seal 34 therebetween and providing a variable volume tubular vessel 4. The bioreactor 2 has means for rotating the tubular vessel 4 about its substantially horizontal longitudinal central axis 10. One or more vessel access ports 18 are provided for transferring materials into and out of the vessel 4. In the embodiment of the invention shown in FIGS. 2 and 3, the bioreactor 2 is made of a tubular vessel 4 with walls 24 constructed at least partially of a gas permeable material 6. The tubular vessel chamber 4 in one preferred embodiment is constructed such that half of it is comprised of gas permeable material 6 and the remaining portion is made of nonpermeable material 7. Preferably, screw threads 38 are provided on the tubular vessel 4 for connecting the tubular vessel 4 to a motor assembly not shown.

Where the variable volume embodiment of the bioreactor 2 is rotated by attachment to a motor assembly that occludes the open end of the first member 30, air ports 36 may be added to the first member 30 to assist with $O_2$ transfer into the tubular vessel chamber. In addition, a shoulder 37 on the first slidably interconnected member 30 may provide a resting place for the drive shaft to rest against when threadably connected to the screw threads in the end 8 of the member 30.

This embodiment of the bioreactor may be made of the same materials as described above for the other embodiments of the bioreactor 2. Preferably, the first tubular member 30 is formed of gas permeable material 6, and the second tubular member 32 is formed of a clear, non-toxic, biocompatible material.

The same means for rotating the tubular vessel 4 may be used as described above, and most preferably by the motor assembly 12 shown in FIG. 1. One or more vessel access ports 18 for transferring materials into and out of the tubular vessel 4 are located on the end 8 of the tubular vessel 4. The volume of the tubular vessel 4 may be varied by the relative movement of the first and second members 30, 32. The vessel members 30, 32 behave as a sliding plunger assembly, similar to a syringe. The seal 34 on the first slidable interconnected member 30 preferably is a rubber gasket, such as an O ring, which may be fitted into a depression around the circumference of the first member 30 near its end 8. The opposing end of the first member 30 is open to allow air or other gases to move freely inside the member 30.

Figure 4:
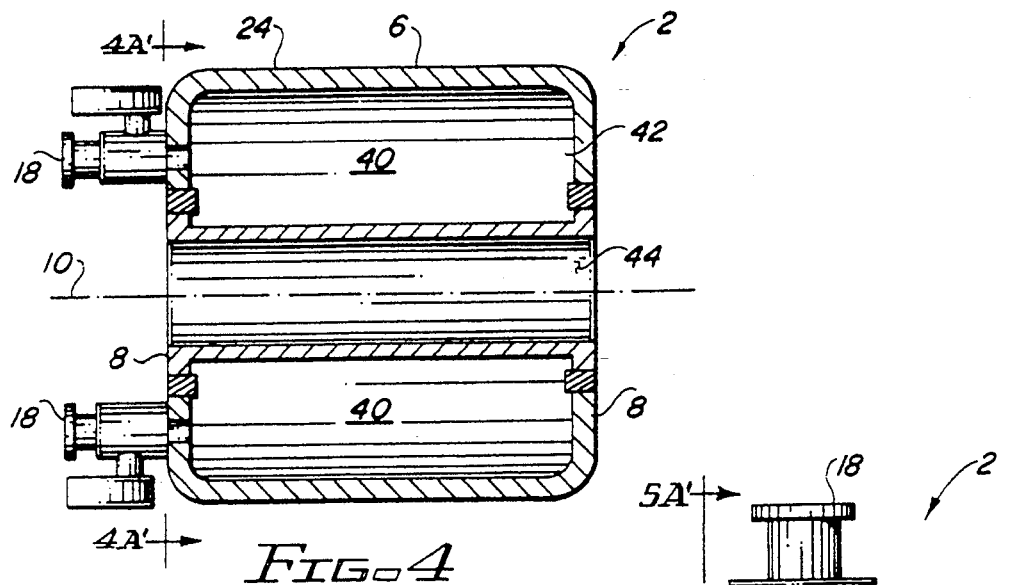
FIG. 4 is a cross-sectional side view of an alternative embodiment of the bioreactor of the present invention which has an annular tubular shape.
Figure 4A:
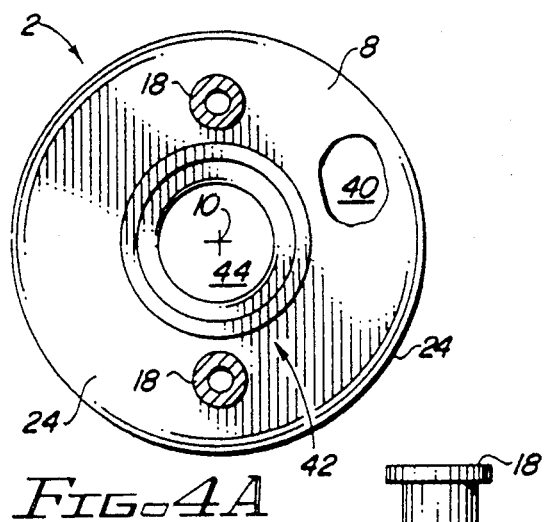
FIG. 4A is an end view of the embodiment of the annular tubular bioreactor of FIG. 4 taken along the line 4A'—4A'.

An alternative embodiment of the bioreactor of the present invention, as shown in FIGS. 4 and 4A, comprises an annular tubular vessel 40 with walls 24 constructed at least partially of a gas permeable material 6 defining an annular vessel chamber 42. It is constructed similarly to the embodiments of the invention described above and varies primarily in its shape. Annular is defined herein to include annular, toroidal, and other substantially symmetrical ring-like shaped tubular vessels 40. The annular vessel 40 has closed ends 8 and a substantially horizontal longitudinal central axis 10. The central portion 44 of the tubular vessel 40, consequently, is left open, allowing air to flow over the central portion 44 of the tubular vessel 40. FIG. 4A is an end view of the embodiment of the bioreactor of FIG. 4 taken along line 4A'—4A'.

Means for rotating the annular tubular vessel 40 about its substantially horizontal longitudinal central axis 10 is preferably a motor assembly 12 as depicted in FIG. 1. Screw threads may be provided in the walls 24 of one end 8 of the central portion 44 of the tubular vessel 40. Other means for rotating the tubular vessel may be used, however, as described above. Two vessel access ports 18, preferably are provided on one end 8 of the tubular vessel 40 to allow cells, medium, and other materials to be transferred into and out of the tubular vessel 40.

Another aspect of the present invention is a method for growing cells in a bioreactor 2 comprising filling a bioreactor 2 constructed at least partially of a gas permeable material 6 with a liquid culture medium and cells; suspending the cells, without appreciable mixing, in the cell medium by rotating the bioreactor 2 about its substantially horizontal longitudinal central axis at a rate that suspends the cells in the liquid culture medium; and continuing rotation of the bioreactor 2 for a time period that permits a desired cell growth.

Referring again to FIG. 1, the bioreactor 2, after sterilization, is filled with a liquid culture medium, such as those commonly known in the art, and cells. If desired, substrate particles may also be added. One preferred microcarrier substrate is collagen coated beads, but numerous types of substrate particles may be used and are known by those skilled in the art. Alternatively, the substrate particles may be pieces of tissue explant. Tissue explant may be diced and added to the culture medium as a substrate upon which cells grow. In addition, tissue explant may be added to a cell culture medium without the addition of other cells. Then, the explant is cultured for further cell growth. In this situation, the tissue explant takes the place functionally of both the cells and the substrate.

Once the tubular vessel 4 is completely filled with medium and any other materials, such that no air spaces exist in the tubular vessel, the cells (or tissue explant if it is cultured instead) are suspended in the bioreactor 2 without any appreciable mixing by rotating the bioreactor 2 about its horizontal longitudinal central axis 10 at a rate that suspends the cells in the liquid culture medium. The appropriate rate of rotation is discussed above.

Rotation of the tubular vessel 4 preferably takes place in the presence of an oxygen containing gas mixture with about 5% carbon dioxide. In the preferred method, the gas mixture is air. In addition, the bioreactor 2 is preferably rotated within an incubator to control the temperature of the tubular vessel 4 culture. The temperature preferably ranges from about 35° C. to about 40° C. for mammalian cells. For any cell, of course, the temperature preferably is maintained at a level that permits cell growth. The rotation of the tubular vessel is continued until the desired amount of cell growth occurs.

During rotation, the oxygen containing gas mixture diffuses through the permeable tubular vessel 4 walls 24 and into the liquid culture medium in the chamber. Carbon dioxide produced by cellular metabolism diffuses through the medium and the walls 24 and is thus eliminated from the chamber. Moreover, the vessel access ports 18 allow the medium in the tubular vessel 4 to be exchanged regularly, if desired. In cases where cells are cultured over longer periods of time, exchanging used culture medium for fresh culture medium becomes more important. Once desired cell growth is obtained, the tubular vessel 4 may be detached from the means for rotation and the cells culture medium may be decanted from the tubular vessel 4 for harvesting of the cells.

The method of the present invention may also be utilized with other embodiments of the bioreactor 2 of the present invention. Such embodiments are described above and claimed herein.

Notwithstanding that the invention is described in terms of particular preferred embodiments, it will be understood that the present invention is not to be construed as limited to such, rather to the lawful scope of the appended claims.

What is claimed is:

1. A gas permeable bioreactor comprising:
a tubular vessel with outer walls constructed at least partially of a gas permeable material, said tubular vessel having closed ends and a substantially horizontal longitudinal central axis;
means for rotating tubular about said substantially horizontal longitudinal central axis;
and one or more vessel access ports for transferring materials into and out the tubular vessel;
wherein the tubular vessel is constructed with a first half comprised of gas permeable material and a second half comprised of a non-gas permeable material.

2. A gas permeable bioreactor comprising:
a tubular vessel with walls constructed at least partially of a gas permeable material, said tubular vessel having closed ends and a substantially horizontal longitudinal central axis;
a permeable membrane positioned across the tubular vessel in a plane substantially perpendicular to the substantially horizontal longitudinal central axis to provide two chambers in said tubular vessel;
means for rotating the tubular vessel about said substantially horizontal longitudinal central axis; and
one or more vessel access ports for transferring materials into and out of the tubular vessel.

3. A gas permeable bioreactor comprising:
a tubular vessel with walls constructed at least partially of a gas permeable material, said tubular vessel having closed ends and a substantially horizontal longitudinal central axis;
wherein one or more microscope viewports are incorporated into a vessel wall;
means for rotating the tubular vessel about said substantially horizontal longitudinal central axis; and
one or more vessel access ports for transferring materials into and out of the tubular vessel.

4. A gas permeable bioreactor comprising:
a tubular vessel with outer walls constructed at least partially of a gas permeable material, said tubular vessel having closed ends and a substantially horizontal longitudinal central axis;
means for rotating the tubular vessel about said substantially horizontal longitudinal central axis;
and one or more vessel access ports for transferring materials into and out of the tubular vessel;
wherein the tubular vessel has means on each end for attaching to an additional bioreactor, whereby a chain of bioreactors may be formed.

5. A gas permeable bioreactor comprising:
a tubular vessel with walls constructed at least partially of a gas permeable material, said tubular vessel having closed ends and a horizontal central axis and having two slidable interconnected members, wherein a first member fits slidably into a second member, forming a liquid tight seal therebetween and providing a variable volume vessel;
means for rotating the tubular vessel about said horizontal central axis; and
one or more vessel access ports for transferring materials into and out of the tubular vessel.

6. The gas permeable bioreactor of claim 5, wherein the gas permeable material is selected from the group consisting of silicone rubber, polytetrafluoroethylene, polyethylene, porous hydrophobic teflon, porous plastics coated with a hydrophobic material, and silicone rubber coated cloth.

7. The gas permeable bioreactor of claim 5, wherein said first and second members are formed of injection molded plastic.

8. The gas permeable bioreactor of claim 5, wherein the means for rotating the tubular vessel is a motor assembly that attaches to the tubular vessel.

9. The gas permeable bioreactor of claim 5, wherein the means for rotating the tubular vessel is a roller mechanism that does not attach to said tubular.

* * * * *